United States Patent [19]

Weidmann et al.

[11] Patent Number: 5,610,172
[45] Date of Patent: Mar. 11, 1997

[54] SULFONAMIDOCARBONYLPYRIDINE-2-CARBOXAMIDES AND PYRIDINE-N-OXIDES WHICH ARE USEFUL AS PHARMACEUTICALS

[75] Inventors: Klaus Weidmann, Kronberg; Martin Bickel, Bad Homburg; Volkmar Günzler-Pukall, Marburg, all of Germany

[73] Assignee: Hoechst Aktiengesellschaft, Frankfurt, Germany

[21] Appl. No.: 410,259

[22] Filed: Mar. 24, 1995

[30] Foreign Application Priority Data

Mar. 25, 1994 [DE] Germany .................. 44 10 423.5

[51] Int. Cl.⁶ .................. C07D 213/81; C07D 213/82; A61K 31/44
[52] U.S. Cl. .................. 514/350; 514/347; 546/293; 546/294; 546/299
[58] Field of Search .................. 546/293.299, 294; 514/347, 350

[56] References Cited

FOREIGN PATENT DOCUMENTS 0562512 9/1993 European Pat. Off. .

Primary Examiner—Zinna Northington Davis
Attorney, Agent, or Firm—Barbara V. Maurer

[57] ABSTRACT

Sulfonamidocarbonylpyridine-2-carboxamides and their pyridine-N-oxides, process for their preparation, and their use as pharmaceuticals The invention relates to sulfonamidocarbonylpyridine-2-carboxamides and their pyridine-N-oxides according to the formula I

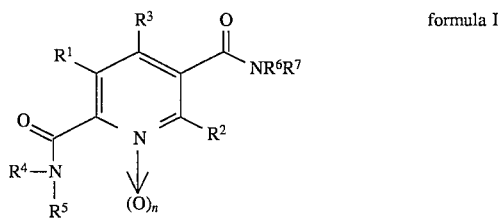

Said compounds are used as pharmaceuticals against fibrotic disorders, as fibrosuppressants and as inhibitors of proline hydroxylase and of collagen biosynthesis.

14 Claims, No Drawings

SULFONAMIDOCARBONYLPYRIDINE-2-CARBOXAMIDES AND PYRIDINE-N-OXIDES WHICH ARE USEFUL AS PHARMACEUTICALS

The invention relates to sulfonamidocarbonylpyridine-2-carboxamides and their pyridine-N-oxides, and to their use as pharmaceuticals against fibrotic disorders.

Compounds which inhibit the enzymes proline hydroxylass and lysine hydroxylass cause a very selective inhibition of collagen biosynthesis by influencing collagen-specific hydroxylation reactions. In the course thereof, protein-bound proline or lysine is hydroxylated by the enzymes proline hydroxylass or lysine hydroxylass. If this reaction is suppressed by inhibitors, a nonfunctional, underhydroxylated collagen molecule results which can be released into the extracellular space by the cells only to a small extent. Additionally, the underhydroxylated collagen cannot be incorporated into the collagen matrix and is very easily degraded by proteolysis. As a consequence of these effects, the amount of collagen deposited extracellularly is on the whole reduced.

Inhibitors of proline hydroxylase are therefore suitable substances in the therapy of disorders in which the deposition of collagens contributes substantially to the clinical picture. These include, inter alia, fibrosis of the lungs, liver and skin (scleroderma) and also atherosclerosis.

It is known that the enzyme proline hydroxylase is effectively inhibited by pyridine-2,4- and -2,5-dicarboxylic acid (K. Majamaa et al., Eur. J. Biochem. 138 (1984) 239–245). In cell culture, however, these compounds are only effective as inhibitors in very high concentrations (Tschank, G. et al., Biochem. J. 238 (1987) 625–633).

DE-A 34 32 094 describes pyridine-2,4- and -2,5-dicarboxylic acid diesters having 1–6 carbon atoms in the ester alkyl moiety as pharmaceuticals for inhibiting proline hydroxylase and lysine hydroxylase.

These lower alkylated diesters, however, have the disadvantage that they are cleaved too rapidly in the body into the acids and do not reach their site of action in the cell in sufficiently high concentration and are thus less suitable for possible administration as pharmaceuticals.

DE-A 37 03 959, DE-A 37 03 962 and DE-A 37 03 963 describe in general form mixed esters/amides, relatively highly alkylated diesters and diamides of pyridine-2,4- and -2,5-dicarboxylic acid, which effectively inhibit collagen biosynthesis in the animal model.

EP-A-0 562 512 describes compounds which have antifibrotic action as a result of the inhibition of proline hydroxylase.

The German application P 44 10 480.4 filed at the same time describes the ester products of the corresponding carboxylic acids of the formula I.

The object was now to seek compounds which inhibit proline hydroxylase even more strongly than the previously known compounds and thus lead to a greater inhibition of collagen biosynthesis.

The object is achieved by the provision of sulfonamidocarbonylpyridine-2-carboxamides and their pyridine-N-oxides of the formula I

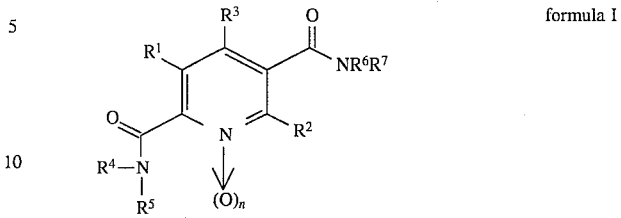

formula I in which $R^1$ is hydroxyl or $(C_1–C_6)$-alkoxy, $R^2$ and $R^3$ are identical or different and are hydrogen, unsubstituted or substituted $(C_1–C_6)$-alkyl, $(C_1–C_6)$-alkoxy, halogen, in particular fluorine, chlorine or bromine, nitrile, hydroxyl or amino, $R^6$ is hydrogen, $(C_1–C_6)$-alkyl or an N-protective group such as $(C_1–C_8)$-alkanoyl, $(C_1–C_6)$-alkylcarbamoyl, $(C_1–C_6)$-alkoxycarbonyl, benzyloxycarbonyl, $(C_1–C_{10})$-acyloxy-$(C_1–C_6)$-alkyl, preferably $(C_1–C_{10})$-alkanoyloxy-$(C_1–C_6)$-alkyl, benzoyloxy-$(C_1–C_6)$-alkyl, benzyloxycarbonyloxy-$(C_1–C_6)$-alkyl or $(C_1–C_6)$-alkoxycarbonyloxy-$(C_1–C_6)$-alkyl, a 1-, 2-, 3- or 4-valent physiologically utilizable cation, in particular $Na^\oplus$, $K^\oplus$, $Mg^{2\oplus}$, $Ca^{2\oplus}$, $Al^{3\oplus}$ or an ammonium ion, optionally substituted 1–3 times by $(C_1–C_8)$-alkyl, $(C_1–C_8)$-hydroxyalkyl, $(C_1–C_4)$-alkoxy-$(C_1–C_8)$-alkyl, phenyl, benzyl or $(C_1–C_8)$ which can be substituted 1 to 3 times by hydroxyl or $(C_1–C_4)$-alkoxy, or a cation of a basic amino acid derivative, $R^7$ is a radical of the formula II, excluding $—SO_2H$,

 (II)

in which

Y is $—SO_2—$ or $—CO—$,

C is a bond or
 a branched or unbranched aliphatic $(C_1–C_{16})$-alkanediyl or cycloaliphatic $(C_3–C_{10})$-alkanediyl radical or a branched or unbranched $(C_2–C_{16})$-alkenediyl or cycloalkenediyl radical, or a $(C_2–C_{16})$-alkynediyl radical or a $(C_2–C_{16})$-alkenynediyl radical, which in each case can contain one or more C—C multiple bonds, U is a bond or hydrogen or a radical from the series of the following heteroatom groups $—CO—$, $—O(CO)—$, $—(CO)—O—$, $—(CO)NR—$, $—NR(CO)—$, $—O—$, $—SO—$, $—SO_2—$, $—NR$, in which R is $(C_1–C_3)$-alkyl or hydrogen, r is 1, 2, 3 or 4, D is a bond or hydrogen or a branched or unbranched aliphatic $(C_1–C_{10})$-alkanediyl radical, or a branched or unbranched $(C_2–C_{10})$-alkenediyl radical, a $(C_2–C_{10})$-alkynediyl radical or a $(C_2–C_{10})$-alkenynediyl radical, which in each case can contain one or more C—C multiple bonds, W is a bond or hydrogen or a $(C_3–C_{10})$cycloaliphatic alkyl, alkenyl, alkynyl or alkenynyl radical or a $(C_6–C_{16})$-aryl radical or a 5- or 6-membered heteroaryl radical, where at least one of the variables C or D or W is not a bond and U is only a heteroatom group if C is not a bond or if D and/or W are not a bond and C and/or W, if these are not a bond or hydrogen, for their part preferably are substituted, $R^4$ is hydrogen, $(C_1-C_6)$-alkyl, phenyl or phenyl-$(C_1-C_4)$-alkyl, $R^5$ is an unsubstituted or substituted, branched or unbranched, aliphatic $(C_1-C_8)$-alkyl radical which carries an acidic group, in particular from the series —$CO_2H$, —$CONHCOR'''$, —$CONHSOR'''$, $CONHSO_2R'''$, —$NHSO_2CF_3$, tetrazolyl, imidazolyl or 3-hydroxyisoxazolyl, where $R'''$ is aryl, heteroaryl, $(C_3-C_7)$-cycloalkyl or $(C_1-C_4)$-alkyl, optionally monosubstituted by $(C_6-C_{12})$-aryl, heteroaryl, OH, SH, $(C_1-C_4)$-alkyl, $(C_1-C_4)$-alkoxy, $(C_1-C_4)$-thioalkyl, -sulfinyl or -sulfonyl, $CF_3$, Cl, Br, F, I, $NO_2$, —COOH, $(C_2-C_5)$-alkoxycarbonyl, $NH_2$, mono- or di-$(C_1-C_4$-alkyl)-amino or $(C_1-C_4)$-perfluoroalkyl, and which can furthermore carry one or more substituents.

Preferred compounds of the formula I are those in which $R^6$ is hydrogen, $(C_1-C_6)$-alkyl or an N-protective group such as $(C_1-C_8)$-alkanoyl, $(C_1-C_6)$-alkylcarbamoyl, $(C_1-C_6)$-alkoxycarbonyl, benzyloxycarbonyl, $(C_1-C_{10})$-acyloxy-$(C_1-C_6)$-alkyl, preferably $(C_1-C_{10})$-alkanoyloxy-$(C_1-C_6)$-alkyl, benzoyloxy-$(C_1-C_6)$-alkyl, benzyloxycarbonyloxy-$(C_1-C_6)$-alkyl or $(C_1-C_6)$-alkoxycarbonyloxy-$(C_1-C_6)$-alkyl, a 1-, 2-, 3- or 4-valent physiologically utilizable cation, in particular $Na^\oplus$, $K^\oplus$, $Mg^{2\oplus}$, $Ca^{2\oplus}$, $Al^{3\oplus}$ or an ammonium ion, optionally substituted 1–3 times by $(C_1-C_8)$-alkyl, $(C_1-C_8)$-hydroxyalkyl, $(C_1-C_4)$-alkoxy-$(C_1-C_8)$-alkyl, phenyl, benzyl or $(C_1-C_8)$-alkyl which can be substituted 1 to 3 times by hydroxyl or $(C_1-C_4)$-alkoxy, or a cation of a basic amino acid derivative, $R^7$ is a radical of the formula II, excluding —$SO_2H$,

$$-Y-[C-U]_r-D-W \quad (II)$$

in which

Y is —$SO_2$— or —CO—,

C is a bond or
a branched or unbranched aliphatic $(C_1-C_{16})$-alkanediyl or cycloaliphatic $(C_3-C_{10})$-alkanediyl radical or a branched or unbranched $(C_2-C_{16})$-alkenediyl or cycloalkenediyl radical, or a $(C_2-C_{16})$-alkynediyl radical or a $(C_2-C_{16})$-alkenynediyl radical, which in each case can contain one or more C—C multiple bonds, U is a bond or hydrogen or a radical from the series of following heteroatom groups —CO—, —O(CO)—, —(CO)—O—, —(CO)NR—, —NR(CO)—, —O—, —SO—, —$SO_2$—, —NR, in which R is $(C_1-C_3)$-alkyl, $(C_1-C_8)$-alkanoyl, $(C_7-C_{16})$-aralkanoyl, $(C_6-C_{12})$-aroyl or hydrogen, r is 1, 2, 3 or 4, D is a bond or hydrogen or a branched or unbranched aliphatic $(C_1-C_{10})$-alkanediyl radical, or a branched or unbranched $(C_1-C_{10})$-alkenediyl radical, a $(C_2-C_{10})$-alkynediyl radical or a $(C_2-C_{10})$-alkenynediyl radical, which in each case can contain one or more C—C multiple bonds, W is a bond or hydrogen or a $(C_3-C_{10})$cycloaliphatic alkyl, alkenyl, alkynyl or alkenynyl radical or a $(C_6-C_{16})$-aryl radical or a 5- or 6-membered heteroaryl radical, where at least one of the variables C or D or W is not a bond and U is only a heteroatom group if C is not a bond or if D and/or W are not a bond and C and/or W, if these are not a bond or hydrogen, for their part preferably are substituted by a combination of up to 5 identical or different substituents from the series hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_6-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —$OCF_2Cl$, —$OCF_2$—$CHFCl$, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynyl carbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxy-carbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-(($C_1-C_{10})$-alkoxy-$(C_1-C_{10})$-alkyl)carbamoyl, N-(($C_6-C_{16})$-aryloxy-$(C_1-C_{10})$-alkyl)carbamoyl, N-(($C_7-C_{16})$-aralkyloxy-$(C_1-C_{10})$-alkyl)carbamoyl, N-$(C_1-C_{10})$-alkyl-N-(($C_1-C_{10})$-alkoxy-$(C_1-C_{10})$-alkyl)carbamoyl, N-$(C_1-C_{10})$-alkyl-N-(($C_6-C_{16})$-aryloxy-$(C_1-C_{10})$-alkyl)carbamoyl, N-$(C_1-C_{10})$alkyl-N-aralkyloxy-$(C_1-C_{10})$-alkyl)carbamoyl, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy N-(($C_1-C_{10})$-alkoxy-$(C_1-C_{10})$-alkyl)carbamoyloxy, N-(($C_6-C_{16})$-aryloxy-$(C_1-C_{10})$-alkyl)carbamoyloxy, N-(($C_7-C_{16})$-aralkyloxy-$(C_1-C_{10})$-alkyl)carbamoyloxy, N-$(C_1-C_{10})$-alkyl-N-(($C_1-C_{10})$-alkoxy-$(C_1-C_{10})$-alkyl)carbamoyloxy, N-$(C_1-C_{10})$-alkyl-N-(($C_6-C_{16})$-aryloxy-$(C_1-C_{10})$-alkyl)carbamoyloxy, N-$(C_1-C_{10})$-alkyl-N-(($C_7-C_{16})$-aralkyloxy-$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenyl-amino, $(C_3-C_{12})$-alkynylamino, N-$(C_6-C_{12})$-arylamino, N-$(C_7-C_{11})$-aralkylamino, N-$(C_1-C_{10})$-alkyl-$(C_7-C_{10})$-aralkylamino, N-$(C_1-C_{10})$-alkyl-N-$(C_6-C_{12})$-arylamino, $(C_1-C_{12})$-alkoxyamino, $(C_1-C_{12})$-alkoxy-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$- alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{16})$-arylsulfamoyl, N-$(C_7-C_{16})$-aralkylsulfamoyl, N-$(C_1-C_{10})$-alkyl-N-$(C_6-C_{16})$-arylsulfamoyl, N-$(C_1-C_{10})$-alkyl-N-$(C_7-C_{16})$-aralkylsulfamoyl, $(C_1-C_{10})$-alkylsulfonamido, N-$((C_1-C_{10})$alkyl)-$(C_1-C_{10})$alkylsulfonamido, $(C_7-C_{16})$-aralkylsulfonamido, N-$((C_1-C_{10})$-alkyl-$(C_7-C_{16})$-aralkylsulfonamido, where the radicals which contain an aryl radical can for their part be substituted on the aryl by 1, 2, 3, 4 or 5 identical or different substituents from the series hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_x C_f H_{(2f+1-g)} F_g$, —$OCF_2Cl$, —$OCF_2$—$CHFCl$, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$arylcarbamoyloxy, N-$(C_1-C_{10})$-alkyl-N-$(C_7-C_{16})$-aralkylcarbamoyloxy N-$((C_1-C_{10})$-alkoxy-$(C_1-C_{10})$-alkyl)carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$-aralkyloxy-$(C_1-C_{10})$alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-$(C_1-C_{10})$-alkyl-N-$(C_7-C_{16})$-aralkylamino, N-$(C_1-C_{10})$-alkyl-N-$(C_6-C_{12})$-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$alkyl, N,N-di-$(C_1-C_{10})$-alkylamino-$(C_1-C_{10})$alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonly, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{16})$-arylsulfamoyl, N-$(C_7-C_{16})$-aralkylsulfamoyl, N-$(C_1-C_{10})$-alkyl-N-$(C_6-C_{16})$-arylsulfamoyl, N-$(C_1-C_{10})$-alkyl-N-$(C_7-C_{16})$-aralkylsulfamoyl, $(C_1-C_{10})$-alkylsulfonamido, N-$((C_1-C_{10})$-alkyl)-$(C_1-C_{10})$-alkylsulfonamido, $(C_7-C_{16})$-aralkylsulfonamido, N-$((C_1-C_{10})$-alkyl-$(C_7-C_{16})$-aralkylsulfonamido, $R^4$ is hydrogen, $(C_1-C_6)$-alkyl, phenyl, phenyl-$(C_1-C_4)$-alkyl, $R^5$ is an unsubstituted or substituted, branched or unbranched, aliphatic $(C_1-C_8)$-alkyl radical which carries a carboxyl group, which is substituted one or more times, preferably once or twice, by a further radical from the series hydroxyl, halogen, cyano, trifluoromethyl, $(C_1-C_{12})$-alkyl, $(C_3-C_8)$-cycloalkyl, $(C_6-C_{12})$-aryl, $(C_7-C_{12})$-aralkyl, $(C_1-C_6)$-alkoxy, $(C_6-C_{12})$-aryloxy, $(C_7-C_{12})$-aralkyloxy, —O—$[CH_2]_x C_f H_{(2f+1-g)} F_g$, where the radicals which contain an aryl radical can for their part be substituted on the aryl by 1, 2, 3, 4 or 5 identical or different substituents from the series hydroxyl, halogen, cyano, trifluoromethyl, nitro, carboxyl, $(C_1-C_6)$-alkyl, $(C_3-C_8)$-cycloalkyl, $(C_1-C_6)$-alkoxy, and n is 0 or 1, f is 1 to 8, preferably 1 to 5, g is 0, 1 to (2f+1) and x is 0 to 8, preferably 0 to 1.

Aryl, aryloxy, heteroaryl and heteroaryloxy compounds are understood as meaning, in particular, phenyl, biphenyl or naphthyl rings or unsubstituted 5- and 6-membered heteroaromatic rings having 1, 2 or 3 nitrogen and/or oxygen and/or sulfur atoms, such as pyridyl, pyridazyl, pyrimidyl, pyrazolyl, imidazolyl, triazolyl, thienyl, oxazolyl and thiazolyl derivatives, and their benzo-fused derivatives.

Of the amino acids mentioned, the natural α-amino acids are in particular preferred.

Among these, preferred compounds of the formula I are those in which $R^1$ is hydroxyl or $(C_1-C_6)$-alkoxy, $R^2$ and $R^3$ are hydrogen $R^6$ is hydrogen, $(C_1-C_6)$-alkyl or an N-protective group such as $(C_1-C_8)$-alkanoyl, $(C_1-C_6)$-alkylcarbamoyl, $(C_1-C_6)$-alkoxycarbonyl, benzyloxycarbonyl, $(C_1-C_{10})$-acyloxy-$(C_1-C_6)$-alkyl, preferably $(C_1-C_{10})$-alkanoyloxy-$(C_1-C_6)$-alkyl, benzoyloxy-$(C_1-C_6)$-alkyl, benzyloxycarbonyloxy-$(C_1-C_6)$-alkyl or $(C_1-C_6)$-alkoxycarbonyloxy-$(C_1-C_6)$-alkyl, a 1-, 2-, 3- or 4-valent physiologically utilizable cation, in particular $Na^{\oplus}$, $K^{\oplus}$, $Mg^{2\oplus}$, $Ca^{2\oplus}$, $Al^{3\oplus}$ or an ammonium ion, optionally substituted 1–3 times by $(C_1-C_8)$-alkyl, $(C_1-C_8)$-hydroxyalkyl, $(C_1-C_4)$-alkoxy-$(C_1-C_8)$-alkyl, phenyl, benzyl or $(C_1-C_8)$-alkyl which can be substituted 1 to 3 times by hydroxyl or $(C_1-C_4)$-alkoxy, or a cation of a basic amino acid derivative, $R^7$ is a radical of the formula II, excluding —$SO_2H$,

in which

Y is —$SO_2$—,

C is a bond, or a branched or unbranched aliphatic $(C_1-C_{16})$-alkanediyl radical, U is a bond or hydrogen or —O—, r is 1, D is a bond or hydrogen or a branched or unbranched aliphatic $(C_1-C_4)$-alkanediyl radical, W is a bond or hydrogen or a $(C_3-C_{10})$-cycloaliphatic alkyl, alkenyl, alkynyl or alkenynyl radical or a $(C_6-C_{16})$-aryl radical or a 5- or 6-membered heteroaryl radical, where at least one of the variables C or D or W is not a bond and U is only a heteroatom group if C is not a bond or if D and/or W are not a bond and C, D and/or W, if these are not a bond or hydrogen, for their part preferably are substituted by a combination of up to 5 identical or different substituents from the series hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_x C_f H_{(2f+1-g)} F_g$, —$OCF_2Cl$, —$OCF_2$—$CHFCl$, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$(C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-$(C_1-C_5)$-alkyl-N-$(C_7-C_{10})$aralkylamino, N-$(C_1-C_5)$-alkyl-N-$(C_6-C_{12})$-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl, where the radicals which contain an aryl radical for their part can be substituted on the aryl by 1, 2, 3, 4 or 5 identical or different substitutents from the series hydrogen, hydroxyl, halogen, cyano, trifluoromethyl, nitro, carboxyl, $(C_1-C_{12})$-alkyl, $(C_3-C_8)$-cycloalkyl, $(C_1-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_x C_f H_{(2f+1-g)} F_g$, —$OCF_2Cl$, —$OCF_2$—$CHFCl$, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$((C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-$(C_1-C_5)$-alkyl-$(C_7-C_{10})$-aralkylamino, N-$(C_7-C_{10})$-alkyl-$(C_6-C_{12})$arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$- alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl, $R^4$ is hydrogen or $(C_1-C_4)$-alkyl, $R^5$ is a branched or unbranched $(C_1-C_4)$-alkyl radical which carries a carboxyl group and which is substituted one or two times by hydroxyl, fluorine, chlorine, $(C_1-C_6)$-alkyl, $(C_3-C_8)$-cycloalkyl, phenyl or benzyl, and n is 0 or 1, f is 1 to 5, g is 0, 1 to (2f+1) and x is 0 or 1.

Particularly preferred compounds of the formula I are those in which $R^1$ is hydroxyl or $(C_1-C_6)$-alkoxy, $R^2$ and $R^3$ are hydrogen, $R^6$ is hydrogen or a 1- or 2-valent physiologically utilizable cation, in particular $Na^\oplus$, $K^\oplus$, $Mg^{2\oplus}$ or $Ca^{2\oplus}$ or an ammonium ion, in particular $H_3N^\oplus C(CH_2OH)_3$, $R^7$ is a radical of the formula II, excluding —$SO_2H$,

$$Y-[C-U]_r-D-W \qquad (II),$$

in which

Y is —$SO_2$—,

C is a bond or a $(C_1-C_{16})$-alkanediyl radical,

U is a bond, r is 1,

D is a bond or hydrogen,

W is hydrogen or a phenyl radical, where at least one of the variables C or D or W is not a bond and C, D and/or W can be substituted by fluorine, chlorine, trifluoromethyl, $(C_1-C_6)$-alkyl, $(C_3-C_8)$-cycloalkyl, benzyl, phenyl, $(C_1-C_8)$-alkoxy, phenoxy or —O—$[CH_2]_xC_fH_{(2f+1-g)}F_g$, carbamoyl, N-$(C_1-C_{10})$-alkylcarbamoyl, N,N-di-$(C_1-C_8)$-alkylcarbamoyl, N-$(C_3-C_8)$-cycloalkylcarbamoyl, N-phenylcarbamoyl, N-$(C_7-C_{11})$-phenylalkylcarbamoyl, N-$(C_1-C_8)$-alkyl-N-$(C_6-C_{16})$-phenylcarbamoyl, N-$(C_1-C_8)$-alkyl-N-$(C_7-C_{11})$-phenylalkylcarbamoyl, N-$((C_1-C_{10})$-alkoxy-$(C_1-C_8)$-alkyl)carbamoyl, N-phenoxy-$(C_1-C_8)$-alkylcarbamoyl, N-$((C_7-C_{16})$-phenylalkyloxy-$(C_1-C_8)$-alkyl)carbamoyl, N-$(C_1-C_8)$-alkyl-N-$((C_1-C_6)$-alkoxy-$(C_1-C_8)$-alkyl)carbamoyl, N-$(C_1-C_8)$-alkyl-N-phenoxy-$(C_1-C_8)$-alkylcarbamoyl, N-$(C_1-C_8)$-alkyl-N-$((C_7-C_{16})$-aralkyloxy-$(C_1-C_{10})$-alkyl)carbamoyl, $(C_1-C_8)$-alkanoylamino, $(C_3-C_8)$-cycloalkanoylamino, phenylamino, $(C_7-C_{11})$-phenylalkanoylamino, $(C_1-C_8)$-alkanoyl-N-$(C_1-C_6)$-alkylamino, $(C_3-C_8)$-cycloalkanoyl-N-$(C_1-C_6)$-alkylamino, benzoyl-N-$(C_1-C_6)$-alkylamino, $(C_7-C_{11})$-phenylalkanoyl-N-$(C_1-C_6)$-alkylamino, $(C_1-C_{10})$-alkanoylamino-$(C_1-C_4)$-alkyl, $(C_3-C_8)$-cycloalkanoylamino-$(C_1-C_4)$-alkyl, phenoylamino-$(C_1-C_6)$-alkyl, $(C_7-C_{11})$-phenylalkanoylamino-$(C_1-C_4)$-alkyl, where the radicals which contain an aryl radical can for their part be substituted on the aryl by 1, 2, 3, 4 or 5 identical or different substituents from the series hydroxyl, carboxyl, $(C_1-C_4)$-alkoxy, phenoxy, benzyloxy, fluorine, chlorine, trifluoromethyl, $(C_1-C_9)$-alkoxycarbonyl, phenoxycarbonyl, $(C_7-C_{11})$-phenylalkoxycarbonyl, $(C_3-C_8)$-cycloalkoxycarbonyl, $(C_1-C_{12})$-alkylcarbonyloxy, $(C_3-C_8)$-cycloalkylcarbonyloxy, benzoyloxy, $(C_7-C_{11})$-phenylalkylcarbonyloxy, $(C_1-C_8)$-alkoxycarbonyloxy, $(C_6-C_{12})$-phenoxycarbonyloxy, $(C_7-C_{11})$-phenylalkyloxycarbonyloxy, $(C_3-C_8)$-cycloalkoxycarbonyloxy, carbamoyl, N-$(C_1-C_6)$-alkylcarbamoyl, N,N-di-$(C_1-C_6)$-alkylcarbamoyl, N-$(C_3-C_8)$-cycloalkylcarbamoyl, N-phenylcarbamoyl, N-$(C_7-C_{11})$-phenylalkylcarbamoyl, hydroxy-$(C_1-C_4)$-alkylcarbamoyl, acyloxy-$(C_1-C_4)$-alkylcarbamoyl, carbamoyloxy, N-$(C_1-C_6)$-alkylcarbamoyloxy, N,N-di-$(C_1-C_6)$-alkylcarbamoyloxy, N-$(C_3-C_8)$-cycloalkylcarbamoyl, $R^4$ is hydrogen, $R^5$ is a methyl group which is substituted by carboxyl and carries a further substituent from the series $(C_1-C_5)$-alkyl, phenyl, benzyl, hydroxyalkyl, hydroxyl, $(C_1-C_4)$-alkoxy, phenoxy or benzyloxy and n is 0 or 1, f is 1 to 5, g is 0, 1 to (2f+1) and x is 0 or 1.

Very particularly preferred compounds of the formula I are those in which $R^1$ is hydroxyl or $(C_1-C_6)$-alkoxy, $R^2$ and $R^3$ are hydrogen, $R^6$ is hydrogen or a 1- or 2-valent physiologically utilizable cation, in particular $Na^\oplus$, $K^\oplus$, $Mg^{2\oplus}$ or $Ca^{2\oplus}$ or an ammoniumion, in particular $H_3N^\oplus C(CH_2OH)_3$, $R^7$ is a radical of the formula II, excluding —$SO_2H$,

$$Y-[C-U]_r-D-W \qquad (II),$$

in which

Y is —$SO_2$—,

C is a bond or $(C_1-C_{16})$-alkanediyl,

U is a bond, r is 1,

D is a bond or hydrogen,

W is a phenyl radical, where W can be substituted once or twice by fluorine, chlorine, $(C_1-C_6)$-alkyl, phenyl or $(C_1-C_6)$-alkoxy, and W is additionally substituted once by phenyl, phenoxy, —O—$[CH_2]_xC_fH_{(2f+1-g)}F_g$, carbamoyl, N-$(C_1-C_{10})$-alkylcarbamoyl, N,N-di-$(C_1-C_8)$-alkylcarbamoyl, N-$(C_3-C_8)$-cycloalkylcarbamoyl, N-phenylcarbamoyl, N-$(C_7-C_{11})$-phenylalkylcarbamoyl, N-$((C_1-C_4)$-alkoxy-$(C_1-C_4)$-alkyl)carbamoyl, N-phenoxy-$(C_1-C_4)$-alkyl)carbamoyl, $(C_1-C_{10})$-alkanoylamino-$(C_1-C_2)$-alkyl, $(C_3-C_8)$-cycloalkanoylamino-$(C_1-C_2)$-alkyl, benzoylamino-$(C_1-C_2)$-alkyl or $(C_7-C_{11})$-phenylalkanoylamino-$(C_1-C_2)$-alkyl, where the radicals which contain an aryl radical can for their part be substituted on the aryl by 1, 2, 3, 4 or 5 identical or different substituents from the series hydroxyl, $(C_1-C_4)$-alkoxy, phenoxy, benzyloxy, fluorine, chlorine, trifluoromethyl, carbamoyl, N-$(C_1-C_6)$-alkylcarbamoyl, N,N-di-$(C_1-C_6)$-alkylcarbamoyl, N-$(C_3-C_8)$-cycloalkylcarbamoyl, N-phenylcarbamoyl, N-$(C_7-C_{11})$-phenalkylcarbamoyl, $R^4$ is hydrogen, $R^5$ is a methyl group which is substituted by carboxyl and n is 0 f is 1 to 5, g is 0, 1 to (2f+1) and x is 0 or 1.

The invention furthermore relates to the use of compounds of the formula I and the physiologically tolerable salts for the production of a pharmaceutical for the inhibition of collagen biosynthesis.

The invention finally relates to the compounds of the formula I for use as pharmaceuticals.

The invention in particular relates to the compounds of the formula I for use as inhibitors of proline-4-hydroxylase.

The invention in particular relates to compounds of the formula I for use as fibrosuppressants.

The invention furthermore comprises prodrugs to the compounds of the formula I, which cause an inhibition of collagen biosynthesis in vivo by release of compounds of the formula I or their salts.

Finally, the invention also comprises prodrugs which in vivo cause an inhibitory action on proline-4-hydroxylase due to release of compounds of the formula I or their salts.

Prodrug groups are chemical groups which in vivo are converted to the carboxylate group of the compounds of the formula I and/or can be removed from the amide N atom and/or can be converted to a pyridine ring.

Suitable prodrug groups are known to the person skilled in the art.

The following prodrug groups may be mentioned in particular:

for the carboxylate group ester, amide or hydroxymethyl groups and their derivatives and aldehyde groups and their derivatives, for the pyridine N atom N-oxides and N-alkyl derivatives and for the pyridine ring 1,4-dihydropyridine derivatives.

The invention furthermore relates to a process for the preparation of compounds of the formula I.

Compounds of the formula I in which Y=SO$_2$, were prepared by i) reacting the pyridine-2-carboxylic acid derivatives or the corresponding esters of the formula 11 with the amines of the formula 5, or ii) reacting the pyridine-5-carboxylic acid
    derivatives of the formula 12 with the sulfonamide derivatives of the formula 9, or iii) reacting the pyridine-5-carboxamide derivatives of the formula 13 with the sulfonic acid derivatives of the formula 2, cf. Scheme 2, where the compounds of the formulae 12 and 13 were for their part prepared from the compounds of the formula 7 by the known methods.

Scheme I illustrates the preparation of compounds of the formula Ia or Ib, in which Y=SO$_2$:

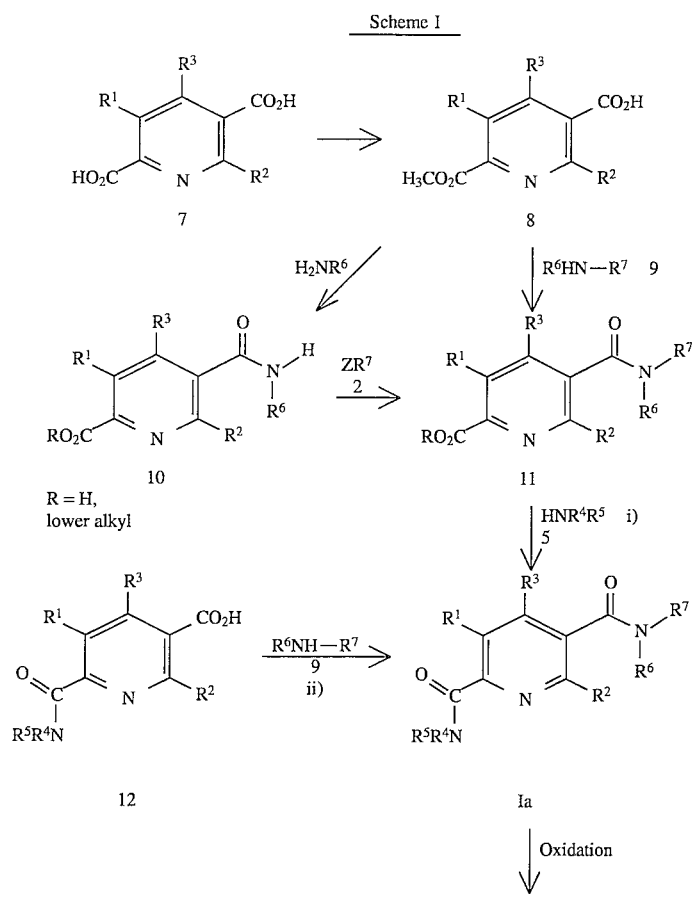

-continued
Scheme I

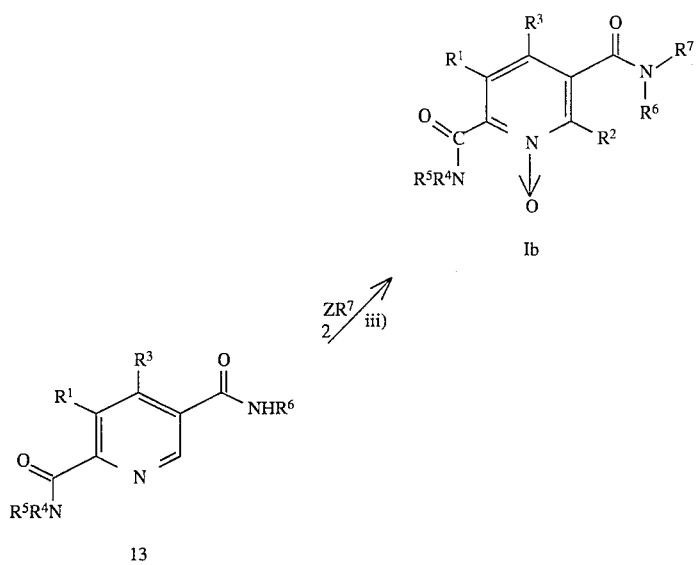

According to CA: Vol. 68, 1968, 68840 h, the pyridine-2-carboxylic acid ester-5-carboxylic acids of the formula 8 can be prepared from the substituted pyridine-2,5-dicarboxylic acids of the formula 7 under esterification conditions. Suitable conditions are e.g. esterification with methanol in the presence of sulfuric acid, the reaction time being selected such that the complete esterification to give the diester product only takes place to a minor extent, or the diester products can be separated off as by-products.

The compounds of the formula 11 are prepared from the compounds of the formula 8 and the sulfonamide derivatives of the formula 9($Y=SO_2$), where it can be expedient to activate both reactants with auxiliary reagents (Houben-Weyl: Methoden der Organischen Chemie, (Methods of Organic Chemistry), Volume IX, Chapter 19, pages 636–637).

Reagents used for carboxylic acid activation can be substances known to the person skilled in the art, such as thionyl chloride, oxalyl chloride, pivaloyl chloride or chloroformic acid ester derivatives. It is not always necessary to isolate these activated derivatives of the compounds of the formula 8. Usually it is expedient to react them with the sulfonamide derivatives of the formula 9 in situ or as a crude product after preparation.

Expediently, the compounds of the formula 9 are first reacted with an inorganic or organic base, such as e.g. sodium or potassium hydroxide, carbonate, alkoxide, hydride or amide, ammonia, triethylamine, tributylamine or pyridine at −20° to +150° C., preferably at 0°–80° C., and this reaction mixture is reacted with a compound of the formula 8 or its activated form. The reaction is carried out in an inert solvent, such as e.g. methylene chloride, methanol, ethanol, acetone, ethyl acetate, toluene, tetrahydrofuran, acetonitrile, N,N-dimethylformamide, N,N-dimethylacetamide, nitromethane, dimethyl sulfoxide or mixtures of these solvents. Alternatively, the esters of the formula 11 can be prepared with the aid of the customary condensing reagents (such as, e.g. N,N'-dicyclohexylcarbodiimide/4-N,N-dimethylaminopyridine).

The reaction of the pyridine-2-carboxylic acid esters 11 with amines $HNR^4R^5$ leads to the compounds of the formula Ia according to the invention.

Alternatively, to prepare the compounds of the formula Ia the compounds 11 (R=lower alkyl) can be hydrolyzed to the pyridine-2-carboxylic acid derivatives 11(R=H) and these can then be coupled with the amines $HNR^4R^5$ according to the customary methods of peptide chemistry to give the compounds of the formula Ia according to the invention.

Further reaction to give the pyridine-N-oxides of the formula Ib is carried out by oxidation of compounds of the formula Ia.

General directions for this oxidation method are also described, for example, in "E. Klinsberg, Pyridine and its Derivatives, Interscience Publishers, New York, 1961, Part 2, 93".

Oxidation with hydrogen peroxide is described, for example, in "E. Ochiai, J. Org. Chem. 18, 534 (1953)".

The process conditions can be inferred in detail from German Patent Application P 38 26 471.4, 38 28 140.6, 39 24 093.2 or 40 01 002.3 and DE-A-37 03 959, 37 03 962 and 37 03 963.

To prepare the compounds of the formula I in which $NR^4R^5$ is a carboxymethyl radical ($NR^4R^5$=NH—$CH_2$—$CO_2H$), the compounds of the formula 11 (R=lower alkyl) were hydrolyzed to the pyridine-2-carboxylic acid derivatives of the formula 11 (R=H) and these were condensed with the appropriate glycine ester derivatives. The carboxymethyl compounds were obtained by hydrolysis of the above ester amides or by catalytic hydrogenation of the benzyl ester amides.

To prepare compounds according to formula I (Ia, Ib) by Scheme 1, compounds are employed in which $R^6$ is hydrogen. Salt formation, according to which $R^6$ is a physiologically utilizable cation, is preferably carried out subsequently. Possible salt-forming agents are preferably N-alkylamines, (hydroxyalkyl)amines and (alkoxyalkyl)amines, such as e.g. 2-ethanolamine, 3-propanolamine, 2-methoxyethylamine, 2-ethoxyethylamine and α,α,α-tris(hydroxymethyl)methylamine (=tris buffer, tromethane) or alternatively basic amino acids, such as e.g. histidine, arginine and lysine.

The introduction of the substituent $R^1$ is illustrated in Scheme 2.

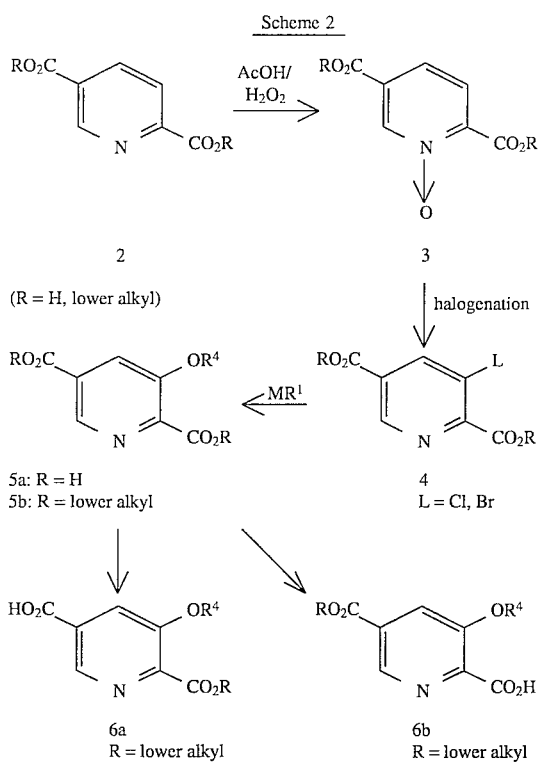

Scheme 2

5a: R = H
5b: R = lower alkyl

4
L = Cl, Br

6a
R = lower alkyl

6b
R = lower alkyl

The 3-substituted 5-carboxypyridine-2-carboxylic esters of the formulae 6a and 6b are prepared from the pyridine-2,5-dicarboxylic acid diesters of the formula 2.

The oxidation of the pyridine-2,5-dicarboxylates of the formula 2 is described in J. Chem. Soc. Perkin Trans. 2, 1978, 34–38 and in J. Org. Chem. 25 (1960) 565–568 (M. L. Peterson).

The halogenation (chlorination) of the pyridine-N-oxides of the formula 3 and the reaction of the 3-chloro-pyridine-2,5-dicarboxylic acid diester (formula 4) with alcoholares $MR^1$ (M=metal; e.g. alkali metal, alkaline earth metal) can be carried out in analogy to the process described in Patent No. CH 658 651 (LONZA).

The pyridine-2-carboxylic acid ester-5-carboxylates of the formulae 6a and 6b can be prepared under esterification conditions from substituted pyridine-2,5-dicarboxylic acids (see CA: Vol. 68, 1968, 68840 h). Suitable conditions are e.g. esterification with methanol in the presence of sulfuric acid, the reaction time being selected such that complete esterification to the diester product only takes place to a minor extent, or the diester products can be separated off as by-products.

The compounds of the formula I are inhibitors of proline-4-hydroxylase. The inhibitors of this enzyme would be determined as described by Kaule and Günzler in Anal. Biochem., 184, 291–297 (1990).

The compounds of the formula I according to the invention have useful pharmacological properties and in particular show antifibrotic activity in particular in the liver, in the lungs and on the skin (scleroderma).

The antifibrotic action can be determined in the carbon tetrachloride-induced liver fibrosis model. For this, rats are treated twice weekly with $CCl_4$ (1 ml/kg)—dissolved in olive oil. The test substance is administered daily, if desired even twice daily, orally or intraperitoneally—dissolved in a suitable tolerable solvent. The extent of liver fibrosis is determined histologically and the amount of collagen in the liver is analyzed by hydroxyproline determination—as described in Kivirikko et al. (Anal. Biochem. 19, 249 f. (1967)). The activity of the fibrinogenesis can be determined by radioimmunological determination of collagen fragments and procollagen peptides in the serum. The compounds according to the invention are active in this model in concentrations of 1–100 mg/kg.

The activity of the fibrinogenesis can be determined by radioimmunological determination of the N-terminal propeptide of collagen type III or of the N- or C-terminal crosslinking domain of collagen type IV (7s-collagen or type IV collagen $NC_1$) in the serum.

For this purpose, the hydroxyproline, procollagen III peptide, 7s-collagen and type IV collagen NC concentrations in the liver of a) untreated rats (control)

b) rats to whom carbon tetrachloride was administered ($CCl_4$ control)

c) rats to whom first $CCl_4$ and then a compound according to the invention was administered were measured (this test method is described by Rouiller, C., Experimental Toxic Injury of the Liver; in The Liver, C. Rouiller, Vol. 2, 5. 335–476, New York, Academic Press, 1964).

The compounds of the formula I can be used as medicaments in the form of pharmaceutical preparations which contain them, if desired together with tolerable pharmaceutical vehicles. The compounds can be used as medicines, e.g. in the form of pharmaceutical preparations which contain these compounds in a mixture with a suitable pharmaceutical, organic or inorganic vehicle for enteral, percutaneous or parenteral administration, such as, e.g. water, gum arabic, gelatin, lactose, starch, magnesium stearate, talc, vegetable oils, polyalkylene glycols, petroleum jelly etc.

For this purpose, they can be administered orally in doses of 0.1–25 mg/kg/day, preferably 1–5 mg/kg/day or parentsrally in doses of 0.01–5 mg/kg/day, preferably 0.01–2.5 mg/kg/day, in particular 0.5–1.0 mg/kg/day. The dose can also be increased in severe cases. In many cases, however, lower doses are also sufficient. These details relate to an adult of about 75 kg in weight.

The invention furthermore comprises the use of the compounds according to the invention in the production of pharmaceuticals which are employed for the treatment and prophylaxis of the abovementioned metabolic disorders.

The invention further relates to pharmaceuticals which contain one or more compounds of the formula I according to the invention and/or their physiologically tolerable salts.

The pharmaceuticals are prepared by processes which are known per se and are familiar to the person skilled in the art. As pharmaceuticals, the pharmacologically active compounds according to the invention (=active substance) are employed either as such or preferably in combination with suitable pharmaceutical auxiliaries or excipients in the form of tablets, coated tablets, capsules, suppositories, emulsions, suspensions or solutions, the active substance content being up to about 95%, advantageously between 10 and 75%.

In addition to solvents, gel-forming agents, suppository bases, tablet auxiliaries and other active substance vehicles, suitable auxiliaries or excipients for the desired pharmaceutical formulation are also, for example, antioxidants, dispersants, emulsifiers, antifoams, flavor correctants, preservatives, solubilizers or colorants.

The following examples are intended to illustrate the invention.

In the following, the compounds are designated as substituted pyridine-2-carboxamides.

They can also be classified as N-substituted glycine derivatives. They are consequently substituted N-(pyridyl-2-carbonyl)glycines.

In this case, the name of the title compound of Example 1 reads, e.g.

N-(3-Methoxy-5-[((phenylsulfonyl)amino)carbonyl] pyridyl-2-carbonyl)glycine

EXAMPLE 1

N-Carboxymethyl-3-methoxy-5-[((phenylsulfonyl) amino)carbonyl]pyridine-2-carboxamide a) 5-Methoxycarbonylpyridine-2-carboxylic acid-1-oxide (cf. J. Org. Chem. 25 (1960) 565)

12 g (60 mmol) of dimethyl pyridine-2,5-dicarboxylate were suspended in 30 ml of glacial acetic acid and treated with 13 ml of hydrogen peroxide (35%) at 20° C. with stirring. The mixture was then heated with stirring to 100° C. (internal temperature), a clear solution being formed at 50° C. After the mixture had been stirred at 100° C. for 90 min, it was allowed to cool to 20° C., the crystalline precipitate was filtered off with suction and washed with water and, after drying, 7.5 g of product were obtained, m.p. 160° C. (dec.).

b) Dimethyl 3-chloropyridine-2,5-dicarboxylate 17 ml of thionyl chloride, 35 ml of anhydrous chloroform and 1.5 ml of N,N-dimethylformamide were heated to 60° C. with stirring and 7.5 g of the above product were added in portions at this temperature. The mixture was then stirred at 60° C. for a further 60 min, the solvent and excess reagent were distilled off in vacuo after cooling, the residue was treated with dichloromethane and the N,N-dimethylformamide×HCl complex was filtered off with suction and washed with dichloromethane. About 15 ml of triethylamine and 10 ml of methanol were added to the mother liquor with cooling and the mixture was stirred for 30 min. After evaporating in vacuo, the residue was dissolved in 50 ml of water and extracted 3×with dichloromethane, the organic phase was dried and concentrated, and the residue was chromatographed on silica gel using n-heptane and n-heptane:ethyl acetate (3:1). 5.3 g of product were crystallized from appropriate fractions using petroleum ether, m.p. 36°–38° C.

c) 3-Methoxypyridine-2,5-dicarboxylic acid 53 g (0.231 mol) of the above diester were dissolved in 500 ml of methanol and treated with 150 ml (0.81 mol) of sodium methoxide solution (30% in methanol) at 20° C. with stirring, the temperature rising to 30° C. The mixture was heated under reflux for 4.5 h, treated with 300 ml of water at 20° C. and stirred at 35° C. for 30 min. The excess methanol was distilled off in vacuo, the aqueous phase was brought to pH 2 with half-concentrated aqueous hydrochloric acid with cooling, and the colorless crystalline product was filtered off with suction and dried. 49 g were obtained, m.p. 185° (evolution of gas); 255° C. (dec.).

d) Methyl 5-carboxy-3-methoxypyridine-2-carboxylate 10 g (50.7 mmol) of the above pyridinedicarboxylic acid were suspended in 150 ml of anhydrous methanol, treated with 2 ml of concentrated sulfuric acid and heated under reflux for 3 h. Half of the methanol was then distilled off in vacuo, the residue was introduced into 400 ml of ice-water, the crystalline residue was filtered off with suction and washed with water, the residue was dissolved in 150 ml of saturated aqueous Na bicarbonate solution, the solution was extracted twice using 80 ml of dichloromethane each time, the bicarbonate phase was brought to pH 1 using half-concentrated aqueous hydrochloric acid with cooling, and the precipitated product was filtered off with suction and dried. 5 g of colorless, crystalline substance were obtained, m.p. 196°–197° C. 1.7 g of dimethyl ester were obtained from the dichloromethane phase, m.p. 53°–55° C. (from petroleum ether).

e) Methyl 3-methoxy-5-[((phenylsulfonyl)amino)carbonyl] pyridine-2-carboxylate 2.4 g (15 mmol) of benzenesulfonamide were suspended in 80 ml of anhydrous tetrahydrofuran and treated at 20° C. with 1.85 g (16.5 mmol) of potassium tert-butoxide with stirring, and the mixture was stirred at 50°–60° C. for 30 min (solution A). In a second flask, 3.2 g (15 mmol) of the above pyridinecarboxylic acid were dissolved in 80 ml of anhydrous tetrahydrofuran, 2.7 g (16.5 mmol) of N,N'-carbonyldiimidazole were added at 20° C. with stirring, the mixture was stirred at 60° C. for 30 min and the cooled solution was then added dropwise to solution A. The mixture was stirred at 60° C. for 1 h and concentrated in vacuo after cooling, and the residue was treated with 200 ml of saturated, aqueous Na bicarbonate solution and extracted with dichloromethane. The bicarbonate phase was brought to pH 3 with half-concentrated aqueous hydrochloric acid and extracted four times with dichloromethane. After drying, dichloromethane was distilled off and the residue was crystallized using diethyl ether/ethyl acetate. 4.0 g of product were obtained, m.p. 160°–163° C. (sintering from 150° C.).

f) 3-Methoxy-5-[((phenylsulfonyl)amino)carbonyl]pyridine-2-carboxylic acid hydrochloride 4.0 g (11.4 mmol) of the above ester were introduced into 150 ml of 1.5N methanolic sodium hydroxide solution at 20° C. with stirring. A short time after a clear solution was formed, the Na salt precipitated. 20 ml of water were added, the mixture was stirred for 30 min and concentrated in vacuo, the residue was dissolved in 100 ml of water, the solution was extracted with dichloromethane, the aqueous phase was brought to pH 1 using concentrated aqueous hydrochloric acid and 3.7 g of product were filtered off with suction as a crystalline precipitate, m.p. 176°–178° C.

g) N-Ethoxycarbonylmethyl-3-methoxy-5-[((phenylsulfonyl)amino)carbonyl]pyridine-2-carboxamide 3.7 g (10 mmol) of the above carboxylic acid were suspended in 300 ml of dichloromethane, treated successively with stirring with 1.4 g (10 mmol) of glycine ethyl ester hydrochloride, 3.9 ml (30 mmol) of N-ethylmorpholine, 1.5 g (11 mmol) of 1-hydroxy-1H-benzotriazole and 4.2 g (10 mmol) of N-cyclohexyl-N'-(2-morpholinoethyl) carbodiimide methyl-p-toluenesulfonate and stirred at 20° C. for 2 days. The insoluble matter was then filtered off with suction, the filtrate was extracted with water and then with 1N aqueous hydrochloric acid, the organic phase was dried and concentrated, and the residue was crystallized using diethyl ether. 1.5 g of product were obtained, m.p. from 100° C. with foaming. A further 1.6 g of product were isolated from the aqueous phase after acidifying with hydrochloric acid to pH 3 and extracting with dichloromethane, drying and concentrating.

h) The title compound was obtained by introducing 700 mg (1.66 mmol) of the above glycine ethyl ester at 20° C. with stirring into 70 ml of 1.5N methanolic sodium hydroxide solution and stirring for 1 hour. The mixture was then concentrated in vacuo, the residue was taken up in 50 ml of water, the mixture was brought to pH 1 using concentrated aqueous hydrochloric acid, and the crystallized product was filtered off with suction and dried. 550 mg of the colorless crystalline title compound were obtained, m.p. 186°–188° C.

EXAMPLE 2

N-Carboxymethyl-5-[((4-(((2-(4-fluorophenyl)ethyl)amino)carbonyl)phenylsulfonyl)amino)carbonyl]-3-methoxy-pyridine-2-carboxamide

EXAMPLE 3

N-Carboxymethyl-5-[((4-(((2-(4-fluorophenyl)ethyl)amino)carbonyl)phenylsulfonyl)amino)carbonyl]-3-(2-methyl-1-propyloxy)pyridine-2-carboxamide

EXAMPLE 4

N-Carboxymethyl-5-[((4-(((2-(4-fluorophenyl)ethyl)amino)carbonyl)phenylsulfonyl)amino)carbonyl]-3-hydroxypyridine-2-carboxamide

EXAMPLE 5

5-[((4-((Cyclohexylamino)carbonyl)phenylsulfonyl)amino)carbonyl]-3-methoxypyridine-2-carboxylic acid N-(carboxymethyl)amide a) 5-[((4-((Cyclohexylamino)carbonyl)phenylsulfonyl)amino)carbonyl]-3-methoxypyridine-2-carboxylic acid 4.2 g (20 mmol) of methyl 5-carboxy-3-methoxypyridine-2-carboxylate (cf. Example 1d) were reacted with 5.6 g (20 mmol) of 4-((cyclohexylamino)carbonyl)benzenesulfonamide analogously to Example 1e) and the product was then hydrolyzed. 7 g of product were obtained, m.p. from 235° C. (sintering at 205° C., from aqueous hydrochloric acid).

b) 5-[((4-((Cyclohexylamino)carbonyl)phenylsulfonyl)amino)carbonyl]-3-methoxypyridine-2-carboxylic acid N-((ethoxycarbonyl)methyl)amide was obtained from 1.85 g (4 mmol) of the above compound analogously to Example 1g); 1.3 g of product, m.p. 225° C. (with foaming, sintering at 185° C., from diisopropyl ether).

c) The title compound was obtained by hydrolyzing 0.55 g of the above ester in 50 ml of 1.5N methanolic NaOH. 0.43 g of product was obtained, m.p. 240° C. (with foaming, sintering from 150° C., from aqueous hydrochloric acid).

EXAMPLE 6

[((4-((Cyclohexylamino)carbonyl)phenylsulfonyl)amino)carbonyl]-3-(2-methyl-1-propyloxy)pyridine-2-carboxylic acid N-(carboxymethyl)amide a) 3-(2-Methyl-1-propyloxy)-pyridine-2,5-dicarboxylic acid Analogously to Example 1c), 3.5 g (146 mmol) of sodium were dissolved in 350 ml of 2-methyl-1-propanol (isobutyl alcohol) and 13.7 g (55 mmol) of dimethyl 3-chloropyridine-2,5-dicarboxylate (prepared as in Example 1b)) were added with stirring at 20° C. The mixture was then stirred at 80° C. for 90 minutes and, after cooling, was concentrated in vacuo, the residue was taken up in 200 ml of 1N methanolic NaOH and the mixture was stirred at 20° C. After 15 minutes the solution became cloudy. Water was added until a clear solution was formed, the aqueous solution was stirred for 1 hour, concentrated in vacuo and acidified with aqueous hydrochloric acid, the crystalline product was filtered off with suction, washed and dried, and 10.6 g of dicarboxylic acid were obtained, m.p. 192° C. (dec.).

b) Methyl 5-carboxy-3-(2-methyl-1-propyloxy)pyridine-2-carboxylate was obtained from the above dicarboxylic acid analogously to Example 1d) by esterification in methanol/sulfuric acid m.p. 158° C. to 160° C. (from aqueous hydrochloric acid).

c) Methyl 5-[((4-((cyclohexylamino)carbonyl)phenylsulfonyl)amino)carbonyl]-3-(2-methyl-1-propyloxy)pyridine-2-carboxylate was obtained from 1.5 g (6 mmol) of the above product using N,N'-carbonyldiimidazole and 4-((cyclohexylamino)carbonyl)benzenesulfonamide (m.p. 268°–269° C., from ethanol/water (1:1)) and potassium tert-butoxide, m.p. 270° C. (from diisopropyl ether).

d) 5-[((4-((Cyclohexylamino)carbonyl)phenylsulfonyl)amino)carbonyl]-3-(2-methyl-1propyloxy)pyridine-2-carboxylic acid was obtained by hydrolysis of the above ester, m.p.>150° C. (with foaming, from aqueous hydrochloric acid).

e) 5-[((4-((Cyclohexylamino)carbonyl)phenylsulfonyl)amino)carbonyl]-3-(2-methyl-1-propyloxy)pyridine-2-carboxylic acid N-((ethoxycarbonyl)methyl)amide was obtained analogously to Example 1g). 1.46 g of product were obtained from 1.55 g (3.1 mmol) of the above carboxylic acid and 0.43 g (3.1 mmol) of glycine ethyl ester hydrochloride, m.p.>280° C. (with evolution of gas, sintering at 135° C., from diethyl ether).

f) The title compound was obtained by hydrolyzing the above ester in methanolic sodium hydroxide solution. Starting from 0.7 g of ester, 0.63 g of the title compound was obtained, m.p. 240° C. (with foaming, sintering at 150° C., from aqueous hydrochloric acid).

EXAMPLE 7

N-Carboxymethyl-5-[((4-((cyclohexylamino)carbonyl)phenylsulfonyl)amino)carbonyl]-3-hydroxypyridine-2-carboxamide

EXAMPLE 8

N-Carboxymethyl-5-[((4-(N,N-diethylaminocarbonyl)phenylsulfonyl)amino)carbonyl]-3-methoxypyridine-2-carboxamide

EXAMPLE 9

N-Carboxymethyl-5-[((4-(N,N-diethylaminocarbonyl)phenylsulfonyl)amino)carbonyl]-3-(2-methyl-1-propyloxy)pyridine-2-carboxamide

EXAMPLE 10

N-Carboxymethyl-5-[((4-(N,N-diethylaminocarbonyl)phenylsulfonyl)amino)carbonyl]-3-hydroxypyridine-2-carboxamide

EXAMPLE 11

N-Carboxymethyl-5-[((4-(N,N-dipropylaminocarbonyl)phenylsulfonyl)amino)carbonyl]-3-methoxyldyridine-2-carboxamide

EXAMPLE 12

N-Carboxymethyl-5-[((4-(4,4-dibutylaminocarbonyl)phenylsulfonyl)amino)carbonyl]-3-methoxypyridine-2-carboxamide

EXAMPLE 13

N-Carboxymethyl-5-[((4-(2-((2-chloro-5-methoxybenzoyl)amino)ethyl)phenylsulfonyl)amino)-carbonyl]-3-methoxypyridine-2-carboxamide

EXAMPLE 14

N-Carboxymethyl-5-[((4-(2-((2-chloro-5-methoxybenzoyl)amino)ethyl)phenylsulfonyl)amino)-carbonyl]-3-(2-methyl-1-propyloxy)pyridine-2-carboxamide

EXAMPLE 15

N-Carboxymethyl-5-[((4-(2-((2-chloro-5-methoxybenzoyl)amino)ethyl)phenylsulfonyl)amino)-carbonyl]-3-hydroxypyridine-2-carboxamide

EXAMPLE 16

N-Carboxymethyl-5-[((4-n-butyloxyphenyl)sulfonyl)amino)carbonyl]-3-methoxypyridine-2-carboxamide

EXAMPLE 17

N-Carboxymethyl-5-[((n-butylsulfonyl)amino)carbonyl]-3-methoxypyridine-2-carboxamide

EXAMPLE 18

N-Carboxymethyl-5-[((4-fluorophenyl)sulfonyl)amino)carbonyl]-3-methoxypyridine-2-carboxamide

EXAMPLE 19

N-Carboxymethyl-3-methoxy-5-[((4-propylphenyl)sulfonyl)amino)carbonyl]pyridine-2-carboxamide

EXAMPLE 20

N-Carboxymethyl-3-hydroxy-5-[((4-propylphenyl)sulfonyl)amino)carbonyl]pyridine-2-carboxamide

EXAMPLE 21

N-Carboxymethyl-5-[((n-butylsulfonyl)amino)carbonyl]-3-(3-methyl-1-butyloxy)pyridine-2-carboxamide

EXAMPLE 22

N-Carboxymethyl-5-[((benzylsulfonyl)amino)carbonyl]-3-methoxypyridine-2-carboxamide

EXAMPLE 23

5-[((1-Decylsulfonyl)amino)carbonyl]-3-methoxypyridine-2-carboxylic acid N-(carboxymethyl)amide a) 5-[((1-Decylsulfonyl)amino)carbonyl]-3-methoxypyridine-2-carboxylic acid 2.1 g (10 mmol) of methyl 5-carboxy-3-methoxypyridine-2-carboxylate (cf. Example 1d)) were reacted with N,N'-carbonyldiimidazole and 1-decylsulfonamide/potassium tert-butoxide in an analogous manner to that described in Example 1e) and the methyl pyridine-2-carboxylate thus obtained was hydrolyzed with 1N methanolic sodium hydroxide solution. After the aqueous solution had been acidified with cooling, 1.4 g of product were obtained, m.p. 145° C. (with dec.).

b) 5-[((1-Decylsulfonyl)amino)carbonyl]-3-methoxypyridine-2-carboxylic acid N-((ethoxycarbonyl)methyl)amide 1 g (2.5 mmol) of the above pyridine-2-carboxylic acid was condensed with glycine ethyl ester hydrochloride in an analogous manner to that described in Example 1g). After working up, the residue was crystallized using diisopropyl ether. 1.1 g of product were obtained, m.p. 70° C.

c) The title compound was obtained by hydrolyzing 0.8 g of the above ester in 100 ml of 1.5N methanolic sodium hydroxide solution at room temperature for 1 hour. The mixture was then concentrated in vacuo, the residue was taken up in water and acidified with hydrochloric acid with ice-cooling, and the precipitate was filtered off with suction, washed with water and dried. 0.52 g of the title compound was obtained, m.p. 90° C.

EXAMPLE 24

5-[((1-Hexadecylsulfonyl)amino)carbonyl]-3-methoxypyridine-2-carboxylic acid N-(carboxymethyl)amide a) Methyl 5-[((1-hexadecylsulfonyl)amino)carbonyl]-3-methoxypyridine-2-carboxylate was obtained from 3.2 g (15 mmol) of methyl 5-carboxy-3-methoxypyridine-2-carboxylate (cf. 1d)) with N,N'-carbonyldiimidazole and 4.8 g (15 mmol) of 1-hexadecylsulfonamide (m.p. 98° to 100° C., from aqueous hydrochloric acid) and potassium tert-butoxide analogously to Example 1e); 6.1 g of product, m.p. 75° to 78° C. (from aqueous hydrochloric acid).

b) 5-[((1-Hexadecylsulfonyl)amino)carbonyl]-3-methoxypyridine-2-carboxylic acid was obtained by hydrolysis of the above ester, m.p. 152° C. (with dec., from ethyl acetate).

c) 5-[((1-Hexadecylsulfonyl)amino)carbonyl]-3-methoxypyridine-2-carboxylic acid N-((ethoxycarbonyl)methyl) amide was obtained analogously to Example 1g), m.p. 127° to 130° C. (with foaming, from diisopropyl ether).

d) The title compound was obtained by hydrolysis of 1.5 g of the above ester analogously to Example 23c). The residue was brought to pH 1 in aqueous tetrahydrofuran using hydrochloric acid and concentrated in vacuo, and the crystalline, somewhat oily product was filtered off with suction and dried, 1.38 g of product, m.p. about 180° C.

What is claimed is:

1. A sulfonamidocarbonylpyridine-2-carboxamide or its pyridine-N-oxide of the formula I

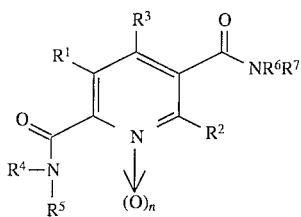

in which $R^1$ is hydroxyl or $(C_1-C_6)$-alkoxy, $R^2$ and $R^3$ are identical or different and are hydrogen, unsubstituted or substituted $(C_1-C_6)$-alkyl, $(C_1-C_6)$-alkoxy, halogen, nitrile, hydroxyl or amino, $R^6$ is hydrogen, $(C_1-C_6)$-alkyl $(C_1-C_8)$-alkanoyl, $(C_1-C_6)$-alkylcarbamoyl, $(C_1-C_6)$-alkoxycarbonyl, benzyloxycarbonyl, $C_1-C_{10}$)-acyloxy-$(C_1-C_6)$-alkyl, benzoyloxy-$(C_1-C_6)$-alkyl, benzyloxycarbonyloxy-$(C_1-C_6)$-alkyl or $(C_1-C_6)$-alkoxycarbonyloxy-$(C_1-C_6)$-alkyl, a 1-, 2-, 3- or 4-valent physiologically utilizable cation, or an ammonium ion, optionally substituted 1–3 times by $(C_1-C_8)$-alkyl, $(C_1-C_8)$-hydroxyalkyl, $(C_1-C_4)$-alkoxy-$(C_1-C_8)$-alkyl, phenyl, benzyl or $(C_1-C_8)$-alkyl which can be substituted 1 to 3 times by hydroxyl or $(C_1-C_4)$-alkoxy, or a cation of a basic amino acid derivative, $R^7$ is a radical of the formula II, excluding —SO$_2$H,

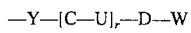

in which

Y is —SO$_2$— or —CO—,

C is a bond or
  a branched or unbranched aliphatic $(C_1-C_{16})$-alkanediyl or cycloaliphatic $(C_3-C_{10})$-alkanediyl radical or a branched or unbranched $(C_2-C_{16})$-alkenediyl or cycloalkenediyl radical, or a $(C_2-C_{16})$-alkynediyl radical or a $(C_2-C_{16})$-alkenynediyl radical, which in each case can contain one or more C—C multiple bonds, U is a bond or hydrogen or —CO—, —O(CO)—, —(CO)—O—, —(CO)NR—, —NR(CO)—, —O—, —SO—, —SO$_2$—, or —NR, in which R is $(C_1-C_3)$-alkyl or hydrogen, r is 1, 2, 3 or 4, D is a bond or hydrogen or a branched or unbranched aliphatic $(C_1-C_{10})$-alkanediyl radical, or a branched or unbranched $(C_2-C_{10})$-alkenediyl radical, a $(C_2-C_{10})$-alkynediyl radical or a $(C_2-C_{10})$-alkenynediyl radical, which in each case can contain one or more C—C multiple bonds, W is a bond or hydrogen or a $(C_3-C_{10})$cycloaliphatic alkyl, alkenyl, alkynyl or alkenynyl radical or a $(C_6-C_{16})$-aryl radical or a 5- or 6-membered heteroaryl radical, where at least one of the variables C or D or W is not a bond and U is only a heteroatom group if C is not a bond or if D and/or W are not a bond and C and/or W, if these are not a bond or hydrogen, are unsubstituted or substituted, $R^4$ is hydrogen, $(C_1-C_6)$-alkyl, phenyl or phenyl-$(C_1-C_4)$-alkyl, $R^5$ is an unsubstituted or substituted, branched or unbranched, aliphatic $(C_1-C_8)$-alkyl radical which carries an acidic group and furthermore can carry one or more substituents.

2. A compound as claimed in claim 1 according to the formula I

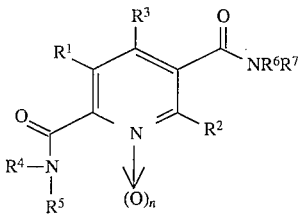

in which $R^1$ is hydroxyl or $(C_1-C_6)$-alkoxy, $R^2$ and $R^3$ are identical or different and are hydrogen, unsubstituted or substituted $(C_1-C_6)$-alkyl, $(C_1-C_6)$-alkoxy, halogen, nitrile, hydroxyl or amino, $R^6$ is hydrogen, $(C_1-C_6)$-alkyl $(C_1-C_8)$-alkanoyl, $(C_1-C_6)$-alkylcarbamoyl, $(C_1-C_6)$-alkoxycarbonyl, benzyloxycarbonyl, $(C_1-C_{10})$-acyloxy-$(C_1-C_6)$-alkyl, benzyloxycarbonyloxy-$(C_1-C_6)$-alkyl or $(C_1-C_6)$-alkoxycarbonyloxy-$(C_1-C_6)$-alkyl, Na$^\oplus$, K$^\oplus$, Mg$^{2\oplus}$, Ca$^{2\oplus}$, Al$^{3\oplus}$ or an ammonium ion, optionally substituted 1–3 times by $(C_1-C_8)$-alkyl, $(C_1-C_5)$-hydroxyalkyl, $(C_1-C_4)$-alkoxy-$(C_1-C_8)$-alkyl, phenyl, benzyl or $(C_1-C_8)$-alkyl which can be substituted 1 to 3 times by hydroxyl or $(C_1-C_4)$-alkoxy, or a cation of a basic amino acid derivative, $R^7$ is a radical of the formula II, excluding —SO$_2$H,

in which

Y is —SO$_2$— or —CO—,

C is a bond or a branched or unbranched aliphatic $(C_1-C_{16})$-alkanediyl or cycloaliphatic $(C_3-C_{10})$-alkanediyl radical or a branched or unbranched $(C_2-C_{16})$-alkenediyl or cycloalkenediyl radical, or a $(C_2-C_{16})$-alkynediyl radical or a $(C_2-C_{16})$-alkenynediyl radical, which in each case can contain one or more C—C multiple bonds, U is a bond, hydrogen, —CO—, —O(CO)—, —(CO)—O—, —(CO)NR—, —NR(CO)—, —O—, —SO—, —SO$_2$—, or —NR, in which R is $(C_1-C_3)$-alkyl, $(C_1-C_8)$-alkanoyl, $(C_7-C_{16})$-aralkanoyl, $(C_6-C_{12})$-aroyl or hydrogen, r is 1, 2, 3 or 4, D is a bond or hydrogen or a branched or unbranched $(C_1-C_{10})$-alkanediyl radical, a $(C_2-C_{10})$-alkynediyl radical or a $(C_2-C_{10})$-alkenynediyl radical, which in each case can contain one or more C—C multiple bonds, W is a bond or hydrogen or a $(C_3-C_{10})$cycloaliphatic alkyl, alkenyl, alkynyl or alkenynyl radical or a $(C_6-C_{16})$-aryl radical or a 5- or 6membered heteroaryl radical, where at least one of the variables C or D or W is not a bond and U is only a heteroatom group if C is not a bond or if D and/or W are not a bond and C and/or W, if these are not a bond or hydrogen, are substituted by a combination of up to 5 identical or different substituents selected from hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$- aryloxy, $(C_7-C_{16})$-aralkyloxy, $(C_1-C_8)$-hydroxyalkyl, —O—$[CH_2]_xC_fH_{(2f+1-g)}F_g$, —OCF$_2$Cl, —OCF$_2$—CHFCl, $(C_1-C_{12})$-alkylcarbonyl, $(C_3-C_8)$-cyclo-alkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-Di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-($(C_1-C_{10})$-alkoxy-$(C_1-C_{10})$-alkyl)carbamoyl, N-($(C_6-C_{16})$-aryloxy-$(C_1-C_{10})$-alkyl)-carbamoyl, N-($(C_7-C_{16})$-aralkyloxy-$(C_1-C_{10})$alkyl)carbamoyl, N-$(C_1-C_{10})$-alkyl-N-($(C_1-C_{10})$-alkoxy-$(C_1-C_{10})$-alkyl)carbamoyl, N-$(C_1-C_{10})$-alkyl-N-($(C_6-C_{16})$-aryloxy-$(C_1-C_{10})$-alkyl)carbamoyl, N-$(C_1-C_{10})$-alkyl-N-($(C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{16})$-arylcarbamoyloxy, N-$(C_1-C_{10})$-alkyl-N-$(C_7-C_{16})$-aralkylcarbamoyloxy N-($(C_1-C_{10})$-alkoxy-$(C_1-C_{10})$-alkyl)-carbamoyloxy, N-($(C_6-C_{16})$-aryloxy-$(C_1-C_{10})$-alkyl)-carbamoyloxy, N-($(C_7-C_{16})$-aralkyloxy-$(C_1-C_{10})$-alkyl)-carbamoyloxy, N-$(C_1-C_{10})$-alkyl-N-($(C_1-C_{10})$-alkoxy-$(C_1-C_{10})$-alkyl)carbamoyloxy, N-$(C_1-C_{10})$-alkyl-N-($(C_6-C_{16})$-aryloxy-$(C_1-C_{10})$-alkyl)carbamoyloxy, N-$(C_1-C_{10})$-alkyl-N-($(C_7-C_{16})$-aralkyloxy-$(C_1-C_{10})$-alkyl)-carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-$(C_1-C_{10})$-alkyl-$(C_7-C_{10})$-aralkylamino, N-$(C_1-C_{10})$-alkyl-N-$(C_6-C_{12})$-arylamino, $(C_1-C_{12})$-alkoxyamino, $(C_1-C_{12})$-alkoxy-$(C_1-C_{10})$-alkylamino, $(C_1-C_{12})$-alkanoylamino, $(C_3-C_8)$-cyclo-alkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto-$(C_1-C_{12})$-alkyl-sulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonly, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{16})$-arylsulfamoyl, N-$(C_7-C_{16})$-aralkylsulfamoyl, N-$(C_1-C_{10})$-alkyl-N-$(C_6-C_{16})$-arylsulfamoyl, N-$(C_1-C_{10})$-alkyl-N-$(C_7-C_{16})$-aralkylsulfamoyl, $(C_1-C_{10})$-alkylsulfonamido, N-($(C_1-C_{10})$-alkyl)-$(C_1-C_{10})$-alkylsulfonamido, $(C_7-C_{16})$-aralkylsulfonamido, N-($(C_1-C_{10})$-alkyl-$(C_7-C_{16})$-aralkylsulfonamido, where the radicals which contain an aryl radical can for their part be substituted on the aryl by 1, 2, 3, 4 or 5 identical or different substituents from selected hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —OCF$_2$Cl, —OCF$_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-($(C_1-C_{10})$-alkoxy-$(C_1-C_{10})$-alkyl)carbamoyl, N-($(C_6-C_{16})$-aryloxy-$(C_1-C_{10})$-alkyl)carbamoyl, N-($(C_7-C_{16})$-aralkyloxy-$(C_1-C_{10})$-alkyl)carbamoyl, N-$(C_1-C_{10})$-alkyl-N-($(C_1-C_{10})$-alkoxy-$(C_1-C_{10})$-alkyl)carbamoyl, N-$(C_1-C_{10})$-alkyl-N-($(C_6-C_{16})$-aryloxy-$(C_1-C_{10})$-alkyl)carbamoyl, N-$(C_1-C_{10})$-alkyl-N-($(C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_2)$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$arylcarbamoyloxy, N-$(C_1-C_{10})$-alkyl-N-$(C_7-C_{16})$-aralkylcarbamoyloxy, N-($(C_1-C_{10})$-alkoxy-$(C_1-C_{10})$-alkyl)carbamoyloxy, N-($(C_6-C_{16})$-aryloxy-$(C_1-C_{10})$-alkyl)carbamoyloxy, N-($(C_7-C_{16})$-aralkyloxy-$(C_1-C_{10})$-alkyl)carbamoyloxy, N-$(C_1-C_{10})$-alkyl-N-($(C_1-C_{10})$-alkoxy-$(C_1-C_{10})$-alkyl) carbamoyloxy, N-$(C_1-C_{10})$-alkyl-N-($(C_6-C_{16})$-aryloxy-$(C_1-C_{10})$-alkyl)carbamoyloxy, N-$(C_1-C_{10})$-alkyl-N-($(C_7-C_{16})$-aralkyloxy-$(C_1-C_{10})$-alkyl)carbamoyloxy, amino, $(C_1-C_{12})$-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-($C_1$–$C_{10}$)-alkyl-N-($C_7$–$C_{16}$)-aralkyl-amino, N-($C_1$–$C_{10}$)-alkyl-N-($C_6$–$C_{12}$)-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkyl-amino-($C_1$–$C_{10}$)-alkyl, N,N-di-($C_1$–$C_{10}$)-alkylamino-($C_1$–$C_{10}$)alkyl, ($C_3$–$C_8$)cycloalkylamino-($C_1$–$C_{10}$)alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-aryl-sulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, sulfamoyl, N-($C_1$–$C_{10}$)-alkylsulfamoyl, N,N-di-($C_1$–$C_{10}$)-alkylsulfamoyl, ($C_3$–$C_8$)-cycloalkylsulfamoyl, N-($C_6$–$C_{16}$)-arylsulfamoyl, N-($C_7$–$C_{16}$)-aralkylsulfamoyl, N-($C_1$–$C_{10}$)-alkyl-N-($C_6$–$C_6$)-arylsulfamoyl, N-($C_1$–$C_{10}$)-alkyl-N-($C_7$–$C_{16}$)-aralkylsulfamoyl, ($C_1$–$C_{10}$)-alkylsulfonamido, N-(($C_1$–$C_{10}$)-alkyl)-($C_1$–$C_{10}$)-alkylsulfonamido, ($C_7$–$C_{16}$)-aralkylsulfonamido, N-(($C_1$–$C_{10}$)-alkyl)-($C_7$–$C_{16}$)-aralkylsulfonamido, $R^4$ is hydrogen, ($C_1$–$C_8$)-alkyl, phenyl, phenyl-($C_1$–$C_4$)-alkyl, $R^5$ is an unsubstitued or substituted branched or unbranched, aliphatic ($C_1$–$C_8$)-alkyl radical which carries a carboxyl group which is substituted once or twice, by hydroxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_1$–$C_6$)-alkoxy, ($C_6$–$C_{12}$)-aryloxy, ($C_7$–$C_{16}$)-aralkyloxy, —O—[$CH_2$]$_x$$C_f$$H_{(2f+1-g)}$$F_g$, where the radicals which contain an aryl radical can for their part be substituted on the aryl by 1, 2, 3, 4 or 5 identical or different substituents selected from hydroxyl, halogen, cyano, trifluoromethyl, nitro, carboxyl, ($C_1$–$C_6$)-alkyl, ($C_3$–$C_8$)-cycloalkyl, ($C_1$–$C_6$)-alkoxy, and n is 0 or 1, f is 1 to 8, g is 0, 1 to (2f+1) and x is 0 to 8.

3. A compound as claimed in claim 1 according to the formula I, in which $R^1$ is hydroxyl or ($C_1$–$C_6$)-alkoxy, $R^2$ and $R^3$ are hydrogen, $R^6$ is hydrogen, ($C_1$–$C_6$)-alkyl ($C_1$–$C_8$)-alkanoyl, ($C_1$–$C_6$)-alkylcarbamoyl, ($C_1$–$C_6$)-alkoxycarbonyl, benzyloxycarbonyl, ($C_1$–$C_{10}$)-alkanoyloxy-($C_1$–$C_6$)-alkyl, benzoyloxy-($C_1$–$C_6$)-alkyl, benzyloxycarbonyloxy-($C_1$–$C_6$)-alkyl or ($C_1$–$C_6$)-alkoxycarbonyloxy-($C_1$–$C_6$)-alkyl, $Na^{\oplus}$, $K^{\oplus}$, $Mg^{2\oplus}$, $Ca^{2\oplus}$, $Al^{3\oplus}$ or an ammonium ion, optionally substituted 1–3 times by ($C_1$–$C_8$)-alkyl, ($C_1$–$C_8$)-hydroxyalkyl, ($C_1$–$C_4$)-alkoxy-($C_1$–$C_8$)-alkyl, phenyl, benzyl or ($C_1$–$C_8$)-alkyl which can be substituted 1 to 3 times by hydroxyl or ($C_1$–$C_4$)-alkoxy, or a cation of a basic amino acid derivative, $R^7$ is a radical of the formula II, excluding —$SO_{02}$H, $$—Y—[C—U]_r—D—W \qquad (II)$$

in which

Y is —$SO_2$—,

C is a bond, or a branched or unbranched aliphatic ($C_1$–$C_{16}$)-alkanediyl radical, U is a bond or hydrogen or —O—, r is 1, D is a bond or hydrogen or a branched or unbranched aliphatic ($C_1$–$C_4$)-alkanediyl radical, W is a bond or hydrogen or a ($C_3$–$C_{10}$)-cycloaliphatic alkyl, alkenyl, alkynyl or alkenynyl radical or a ($C_6$–$C_{16}$)-aryl radical or a 5- or 6-membered heteroaryl radical, where at least one of the variables C or D or W is not a bond and U is only a heteroatom group if C is not a bond or if D and/or W are not a bond and C, D and/or W, if these are not a bond or hydrogen, are substituted by a combination of up to 5 identical or different substituents selected from hydroxyl, halogen, cyano, trifluoromethyl, nitro, carboxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_6$–$C_{12}$)-aryloxy, ($C_7$–$C_{16}$)-aralkyloxy, ($C_1$–$C_8$)-hydroxyalkyl, —O—[$CH_2$]$_x$$C_f$$H_{(2f+1-g)}$$F_g$, —$OCF_2Cl$, —$OCF_2$—$CHFCl$, ($C_1$–$C_{12}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, cinnamoyl, ($C_3$–$C_{12}$)-alkenylcarbonyl, ($C_3$–$C_{12}$)-alkynylcarbonyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_3$–$C_{12}$)-alkenyloxycarbonyl, ($C_3$–$C_{12}$)-alkynyloxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_3$–$C_{12}$)-alkenylcarbonyloxy, ($C_3$–$C_{12}$)-alkynylcarbonyloxy, carbamoyl, N-($C_1$–$C_{12}$)-alkylcarbamoyl, N,N-di-($C_1$–$C_{12}$)-alkylcarbomoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-($C_1$–$C_5$)-alkyl-N-($C_7$–$C_{10}$)-aralkylamino, N-($C_1$–$C_5$)-alkyl-N-($C_6$–$C_{12}$)-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalk-anoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_2$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, where the radicals which contain an aryl radical for their part can be substituted on the aryl by 1, 2, 3, 4 or 5 identical or different substituents selected from hydrogen, hydroxyl, halogen, cyano, trifluoromethyl, nitro, carboxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_6$–$C_{12}$)-aryloxy, ($C_7$–$C_{16}$)-aralkyloxy, ($C_1$–$C_8$)-hydroxyalkyl, —O—[$CH_2$]$_x$$C_f$$H_{(2f+1-g)}$$F_g$, —$OCF_2Cl$, —$OCF_2$—$CHFCl$, ($C_1$–$C_{12}$)-alkylcarbonyl, ($C_3$–$C_8$)-cyclo-alkylcarbonyl, ($C_6$–$C_{12}$)-arylcarbonyl, ($C_7$–$C_{16}$)-aralkylcarbonyl, cinnamoyl, ($C_3$–$C_{12}$)-alkenylcarbonyl, ($C_3$–$C_{12}$)-alkynylcarbonyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl , ($C_3$–$C_8$)-cycloalkoxycarbonyl, ($C_3$–$C_{12}$)-alkenyloxycarbonyl, ($C_3$–$C_{12}$)-alkynyloxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_3$–$C_{12}$)-alkenylcarbonyloxy, ($C_3$–$C_{12}$)-alkynylcarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-($C_1$–$C_5$)-alkyl-($C_7$–$C_{10}$)-aralkylamino, N-($C_1$–$C_5$)-alkyl-($C_6$–$C_{12}$)-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkyl-sulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, $R^4$ is hydrogen or ($C_1$–$C_4$)-alkyl, $R^5$ is a branched or unbranched ($C_1$–$C_4$)-alkyl radical which carries a carboxyl group and which is substituted one or two times by hydroxyl, fluorine, chlorine, ($C_1$–$C_6$)-alkyl, ($C_3$–$C_8$)-cycloalkyl, phenyl and benzyl, and n is 0 or 1, f is 1 to 5, g is 0, 1 to (2f+1) and x is 0 or 1.

4. A compound as claimed in claim 3 according to the formula I, in which $R^1$ is hydroxyl or ($C_1$–$C_6$)-alkoxy, $R^2$ and $R^3$ are hydrogen, $R^6$ is hydrogen or $Na^{\oplus}$, $K^{\oplus}$, $Mg^{2\oplus}$ or $Ca^{2\oplus}$ or an ammonium ion, $R^7$ is a radical of the formula II, excluding —$SO_2H$, $$Y—[C—U]_r—D—W \qquad (II),$$

in which

Y is —$SO_2$—,

C is a bond or a ($C_1$–$C_6$)-alkanediyl radical,

U is a bond, r is 1,

D is a bond or hydrogen,

W is hydrogen or a phenyl radical, where at least one of the variables C or D or W is not a bond and C, D and/or W can be substituted by fluorine, chlorine, trifluoromethyl, ($C_1$–$C_{16}$)-alkyl, ($C_3$–$C_8$)-cycloalkyl, benzyl, phenyl, ($C_1$–$C_6$)-alkoxy, phenoxy or —O—[$CH_2$]$_x$$C_f$$H_{(2f+1g)}$$F_g$, carbamoyl, N-($C_1$–$C_{10}$)-alkylcarbamoyl, N,N-di-($C_1$–$C_8$)-alkylcarbamoyl, N-($C_3$–$C_8$)-cycloalkylcarbamoyl, N-phenylcarbamoyl, N-($C_7$–$C_{11}$)-phenylalkylcarbamoyl, N-($C_1$–$C_8$)-alkyl-N-($C_6$–$C_{16}$)-phenylcarbamoyl, N-($C_1$–$C_8$)-alkyl-N-($C_7$–$C_{11}$)-phenylalkylcarbamoyl, N-(($C_1$–$C_{10}$)-alkoxy-($C_1$–$C_{10}$)-alkylcarbamoyl, N-phenoxy-($C_1$–$C_8$)-alkylcarbamoyl, N-(($C_7$–$C_{16}$)-phenylalkyloxy-($C_1$–$C_8$)-alkylcarbamoyl, N-($C_1$–$C_8$)-alkyl-N-(($C_1$–$C_6$)-alkoxy-($C_1$–$C_8$)-alkyl) carbamoyl, N-($C_1$–$C_8$)-alkyl-N-phenoxy-($C_1$–$C_8$)-alkylcarbamoyl, N-($C_1$–$C_8$)-alkyl-N-(($C_7$–$C_{16}$)-aralkyloxy-($C_1$–$C_{10}$)-alkylcarbamoyl, ($C_1$–$C_{10}$)-alkanoylamino, ($C_3$–$C_8$)-cycloalkanoylamino, phenylamino, ($C_7$–$C_{11}$)-phenylalkanoylamino, ($C_1$–$C_8$)-alkanoyl-N-($C_1$–$C_{10}$)-alkylamino, ($C_3$–$C_8$)-cycloalkanoyl-N-($C_1$–$C_6$)-alkylamino, benzoyl-N-($C_1$–$C_6$)-alkylamino, ($C_7$–$C_{11}$)-phenylalkanoyl-N-($C_1$–$C_{10}$)-alkylamino, ($C_1$–$C_{10}$)-alkanoylamino-($C_1$–$C_4$)-alkyl, ($C_3$–$C_8$)-cycloalkanoylamino-($C_1$–$C_4$)-alkyl, phenoylamino-($C_1$–$C_6$)-alkyl, ($C_7$–$C_{11}$)-phenylalkanoylamino-($C_1$–$C_6$)-alkyl, where the radicals which contain an aryl radical can for their part be substituted on the aryl by 1, 2, 3, 4 or 5 identical or different substituents selected from hydroxyl, fluorine, chlorine, trifluoro-methyl, carboxyl, ($C_1$–$C_4$)-alkoxy, benzyloxy, phenoxy, ($C_1$–$C_{12}$)-alkoxycarbonyl, ($C_3$–$C_8$)-cycloalkylcarbonyl, phenoxycarbonyl, ($C_7$–$C_{11}$)-phenylalkoxycarbonyl, (C₁–C₁₂)-alkylcarbonyloxy, (C₃–C₈)-cycloalkylcarbonyloxy, benzyloxy, (C₇–C₁₁)-phenylalkylcarbonyloxy, carbamoyl, N-(C₁–C₆)-alkylcarbamoyl, N,N-di-(C₁–C₆)-alkylcarbamoyl, N-(C₃–C₈)-cycloalkylcarbamoyl, N-phenylcarbamoyl, N-(C₇–C₁₁)-phenylalkylcarbamoyl, hydroxy-(C₁–C₄)-alkylcarbamoyl, acyloxy-(C₁–C₄)-alkylcarbamoyl, carbamoyloxy, N-(C₁–C₆)-alkylcarbamoyloxy, N,N-di-(C₁–C₆)-alkylcarbamoyloxy, N-(C₃–C₈)-cycloalkylcarbamoyl, R⁴ is hydrogen, R⁵ is a methyl group which is substituted by carboxyl and has a further substituent selected from hydroxyl, hydroxy-(C₁–C₄)-alkyl, phenyl, benzyl, (C₁–C₄)-alkoxy, (C₁–C₅)-alkyl, benzyloxy or phenoxy and n is 0 or 1, f is 1 to 5, g is 0, (2f+1) and x is 0 or 1.

5. A compound as claimed in claim 1 to 4 of the formula I, in which

R¹ is hydroxyl or (C₁–C₆)-alkoxy,

R² and R³ are hydrogen,

R⁶ is hydrogen or a Na⁺, K⁺, Mg²⁺ or Ca²⁺ or H₃N⁺C(CH₂OH)₃,

R⁷ is a radical of the formula II, excluding —SO₂—,

Y—[C—U]ᵣ—D—W (II), 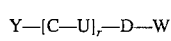

in which

Y is Y —SO₂—,

C is a bond or (C₁–C₁₆)-alkanediyl,

U is a bond, r is 1,

D is a bond or hydrogen,

W is a phenyl radical, where W can be substituted once or twice by fluorine, chlorine, (C₁–C₆)-alkyl or (C₇–C₁₆)-aralkyl, phenyl and (C₁–C₆)-alkoxy and W is additionally substituted once by phenyl, phenoxy, —O—[CH₂]ₓCfH₍₂f₊₁₋g₎Fg, carbamoyl, N-(C₁–C₁₀)-alkylcarbamoyl, N,N-di-(C₁–C₈)-alkylcarbamoyl, N-(C₃–C₈)-cycloalkylcarbamoyl, N-phenylcarbamoyl, N-(C₇–C₁₁)-phenylalkylcarbamoyl, N-((C₁–C₄)-alkoxy-(C₁–C₄)-alkyl)-carbamoyl, N-phenoxy-(C₁–C₄)-alkylcarbamoyl, (C₁–C₁₀)-alkanoylamino-(C₁–C₂)-alkyl, (C₃–C₈)-cycloalkanoylamino-(C₁–C₂)-alkyl, benzoylamino-(C₁–C₂)-alkyl or (C₇–C₁₁)-phenylalkanoylamino-(C₁–C₂)-alkyl, where the radicals which contain an aryl radical can for their part be substituted on the aryl by 1, 2, 3, 4 or 5 identical or different substituents selected from hydroxyl, carboxyl, (C₁–C₄)-alkoxyl, phenoxy, benzyloxy, fluorine, chlorine, trifluoromethyl, carbamoyl, N-(C₁–C₆)-alkylcarbamoyl, N,N-di-(C₁–C₆)-alkylcarbamoyl, N-(C₃–C₈)-cycloalkylcarbamoyl, N-phenylcarbamoyl, N-(C₇–C₁₁)-phenalkylcarbamoyl, R⁴ is hydrogen, R⁵ is a methyl group which is substituted by carboxyl, and n is 0, f is 1 to 5, g is 0, 1 to (2f+1) and x is 0 or 1.

6. A method for the treatment of disorders of the metabolism of collagen and collagen-like substances which comprises administering to a patient in need thereof a collagen biosynthesis inhibiting amount of the compound of claim 1.

7. A method for the treatment of fibrotic disorders which comprises administering to a patient in need thereof a proline hydroxylase inhibiting amount of the compound of claim 1.

8. The compound of claim 5, wherein R¹ is hydroxy or (C₁–C₆) alkoxy; R² and R³ are hydrogen; R⁶ is hydrogen, and R⁷ is —SO₂ phenyl wherein the phenyl group is optionally substituted by carbamoyl or N-(C₃–C₈)cycloalkylcarbamoyl.

9. The compound of claim 8 which is N-carboxymethyl-3-methoxy-5-[((phenylsulfonyl)amino)-carbonyl]pyridine-2-carboxamide.

10. The compound of claim 8 which is 5-[((4-((cyclohexylamino)carbonyl)phenylsulfonyl)amino)-carbonyl]-3-methoxypyridine-2-carboxylic acid N-(carboxymethyl)amide.

11. The compound of claim 8 which is 5-[((4-((cyclohexylamino)carbonyl)phenylsulfonyl)amino)-carbonyl]-3-(2-methyl-1-propyloxy)pyridine-2-carboxylic acid N-(carboxymethyl)amide.

12. A method for inhibiting fibrosis which comprising administering to a patient in need thereof a fibrosis inhibiting amount of the compound of claim 1.

13. A method for inhibiting proline hydroxylase which comprises administering to a patient in need thereof a proline hydroxylase inhibiting amount of the compound of claim 1.

14. A pharmaceutical composition which comprises a pharmaceutically acceptable carrier and a pharmaceutically effective amount of the compound of claim 1.

* * * * *